(12) United States Patent
Walters

(10) Patent No.: US 12,002,564 B2
(45) Date of Patent: Jun. 4, 2024

(54) SYSTEM AND METHOD FOR PREDICTING INDIVIDUAL PERFORMANCE IN A SPORTING ACTIVITY

(71) Applicant: Rijjin, Inc., Walnut, CA (US)

(72) Inventor: Derin Walters, Tokyo (JP)

(73) Assignee: Rijjin, Inc., Walnut, CA (US)

( * ) Notice: Subject to any disclaimer, the term of this patent is extended or adjusted under 35 U.S.C. 154(b) by 123 days.

(21) Appl. No.: 17/808,806

(22) Filed: Jun. 24, 2022

(65) Prior Publication Data

US 2023/0420102 A1 Dec. 28, 2023

(51) Int. Cl.
*G16H 20/30* (2018.01)

(52) U.S. Cl.
CPC .................................. *G16H 20/30* (2018.01)

(58) Field of Classification Search
CPC ................ G16H 20/30; A63B 24/0021; A63B 24/0062; A63B 24/0075; A63B 2024/0025; A63B 2024/0056; A63B 2024/0065; A63B 2024/0068; A63B 2024/0078; A63B 2024/0081; A63B 2230/04; A63B 2230/06
See application file for complete search history.

(56) References Cited

U.S. PATENT DOCUMENTS 9,750,415 B2 * 9/2017 Breslow ............... A61B 5/7278
9,788,785 B2 * 10/2017 LeBoeuf ............... A61B 5/0077
9,829,327 B2 * 11/2017 Nagy ................. A63B 24/0075
10,112,075 B2 * 10/2018 Wisbey ................ G16H 40/63
10,660,534 B2 * 5/2020 Lee ..................... A61B 5/02438
11,410,765 B2 * 8/2022 Ahmed ............... A61B 5/02427
11,690,564 B2 * 7/2023 Carpenter .......... A63B 24/0075
2012/0035021 A1 2/2012 Saalasti et al.
2014/0213858 A1 7/2014 Presura et al.
(Continued)

FOREIGN PATENT DOCUMENTS

| | | |
|---|---|---|
| CN | 107924716 | 4/2018 |
| EP | 3733068 | 11/2020 |
| TW | 201733520 | 10/2017 |

OTHER PUBLICATIONS

PCT International Application No. PCT/US23/68276, International Search Report and Written Opinion of the International Searching Authority, dated Sep. 29, 2023, 6 pages.
(Continued)

*Primary Examiner* — Joshua Lee
(74) *Attorney, Agent, or Firm* — DLA PIPER LLP (US)

(57) ABSTRACT

A computing system receives, from a user device, a request to generate an estimated activity profile for a user of the user device for a workout. The computing system identifies route information for the workout. The computing system generates, via a trained prediction system, an initial estimated heartrate for the user based on a personalized training process for the user. The computing system generates, via the trained prediction system, a duration of a portion of the workout based on the route information and environmental information associated with a time and day of the workout. The computing system generates, via the trained prediction system, a projected heartrate of the user during the workout based on the initial estimated heartrate of the user and the generated duration. The computing system outputs the estimated activity profile corresponding to the workout based on the projected heartrate of the user.

20 Claims, 12 Drawing Sheets

(56) References Cited

U.S. PATENT DOCUMENTS

| | | |
|---|---|---|
| 2015/0250396 A1 | 9/2015 | Ahmed et al. |
| 2016/0209225 A1* | 7/2016 | Nagy .................... G16H 20/30 |
| 2017/0216671 A1* | 8/2017 | Wisbey ............. A61B 5/02438 |
| 2019/0186919 A1 | 6/2019 | Lush et al. |
| 2021/0153805 A1* | 5/2021 | Carpenter ............ A61B 5/1118 |

OTHER PUBLICATIONS

Ni, et al., "Modeling heart rate and activity data for personalized fitness recommendation," The World Wide Web Conference, May 2019, pp. 1343-1353.

Ludwig, et al., "A Convolution Model for Heart Rate Prediction in Physical Exercise," icSPORTS, 2016, pp. 157-164.

Office Action of Taiwanese Application No. 112123323, mailed Mar. 13, 2024, 6 pages.

\* cited by examiner

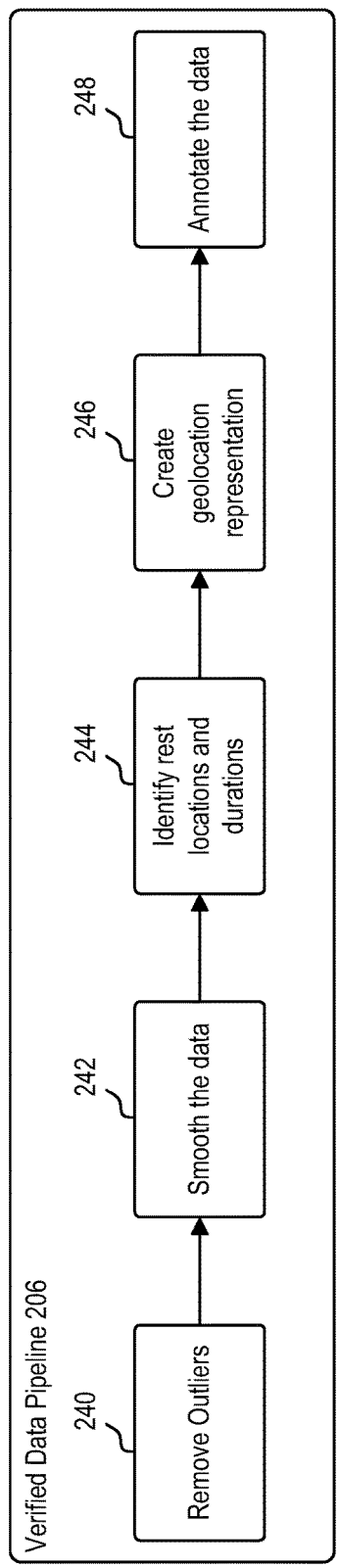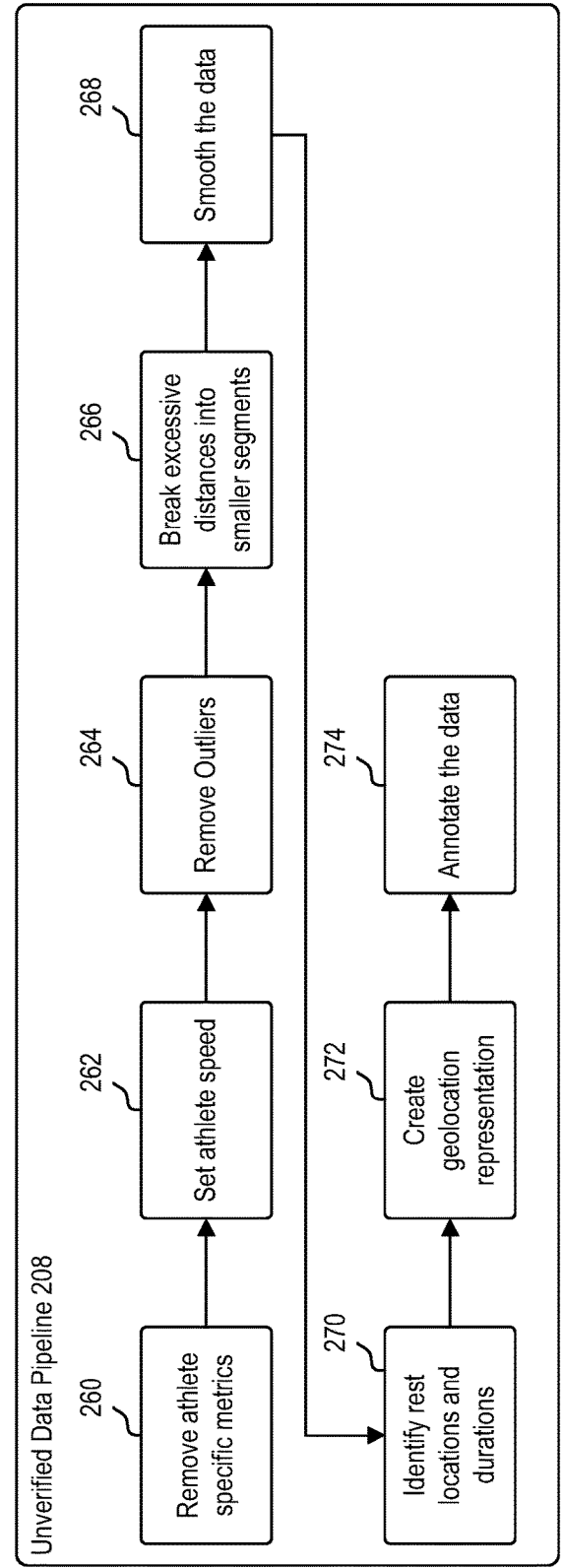

SYSTEM AND METHOD FOR PREDICTING INDIVIDUAL PERFORMANCE IN A SPORTING ACTIVITY

FIELD OF DISCLOSURE

The present disclosure generally relates to a system and method for predicting individual performance of a sporting activity, according to example embodiments.

BACKGROUND

With the proliferation of wearable devices and fitness trackers, it has become commonplace for athletes and fitness enthusiasts to be able to track their workouts to identify trends or improvements in their fitness abilities. Such devices provide users with real-time or near real-time feedback regarding biometric data, such as their heartrate, as well as other metrics, such as cadence.

SUMMARY

In some embodiments, a method is disclosed herein. A computing system receives, from a user device, a request to generate an estimated activity profile for a user of the user device for a workout. The computing system identifies route information for the workout. The route information includes at least one data point associated with the route information. The computing system generates, via a trained prediction system, an initial estimated heartrate for the user for the at least one data point in the route information based on a personalized training process for the user. The computing system generates, via the trained prediction system, a duration of a portion of the workout based on the at least one data point in the route information and environmental information associated with a time and day of the workout. The computing system generates, via the trained prediction system, a projected heartrate of the user during the workout based on the initial estimated heartrate of the user and the generated duration. The computing system outputs the estimated activity profile corresponding to the workout based on the projected heartrate of the user. The estimated activity profile includes the projected heartrate of the user.

In some embodiments, a non-transitory computer readable medium is disclosed herein. The non-transitory computer readable medium includes one or more sequences of instructions, which, when executed by a processor, causes a computing system to perform operations. The operations include receiving, by the computing system from a user device, a request to generate an estimated activity profile for a user of the user device for a workout. The operations further include identifying, by the computing system, route information for the workout. The route information includes at least one data point associated with the route information. The operations further include generating, by the computing system via a trained prediction system, an initial estimated heartrate for the user for the at least one data point in the route information based on a personalized training process for the user. The operations further include generating, by the computing system via the trained prediction system, a duration of a portion of the workout based on the at least one data point in the route information and environmental information associated with a time and day of the workout. The operations further include generating, by the computing system via the trained prediction system, a projected heartrate of the user during the workout based on the initial estimated heartrate of the user and the generated duration. The operations further include outputting, by the computing system, the estimated activity profile corresponding to the workout based on the projected heartrate of the user. The estimated activity profile includes the projected heartrate of the user.

In some embodiments, a system is disclosed herein. The system includes a processor and a memory. The memory has programming instructions stored thereon, which, when executed by the processor, causes the system to perform operations. The operations include receiving, from a user device, a request to generate an estimated activity profile for a user of the user device for a workout. The operations further include identifying route information for the workout. The route information includes at least one data point associated with the route information. The operations further include generating, via a trained prediction system, an initial estimated heartrate for the user for the at least one data point in the route information based on a personalized training process for the user. The operations further include generating, via the trained prediction system, a duration of a portion of the workout based on the at least one data point in the route information and environmental information associated with a time and day of the workout. The operations further include generating, via the trained prediction system, a projected heartrate of the user during the workout based on the initial estimated heartrate of the user and the generated duration. The operations further include outputting the estimated activity profile corresponding to the workout based on the projected heartrate of the user. The estimated activity profile includes the projected heartrate of the user.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

FIG. 2B is a block diagram illustrating a verified data pipeline of the pre-processing system of FIG. 2A, according to example embodiments.

FIG. 2C is a block diagram illustrating an unverified data pipeline of the pre-processing system of FIG. 2A, according to example embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Estimating fitness performance is a topic of interest to athletes and coaches alike at all ability levels. Conventional approaches to estimating fitness performance tend to focus on a single element of performance. For example, conventional approaches may focus on predicting a race result from a known shorter distance, estimating maximum heart rate versus age, understanding effects of treadmill incline on speed, and the like. These conventional approaches are limited in that they fail to take a holistic personalized view of estimating fitness for each athlete.

One or more techniques described herein improve upon conventional approaches by utilizing a machine learning approach in which relevant metrics from activity tracking devices may be analyzed to predict fitness performance for an activity or workout, while also controlling for multivariate effects of the physical environment, climate, training load, and physiological limitations such as aging. For example, one or more techniques described herein may generate a predicted or estimated activity file for the activity or workout. In some embodiments, the predicted or estimated activity file may be based on, for example, location coordinates associated with the activity or workout.

Figure 1:
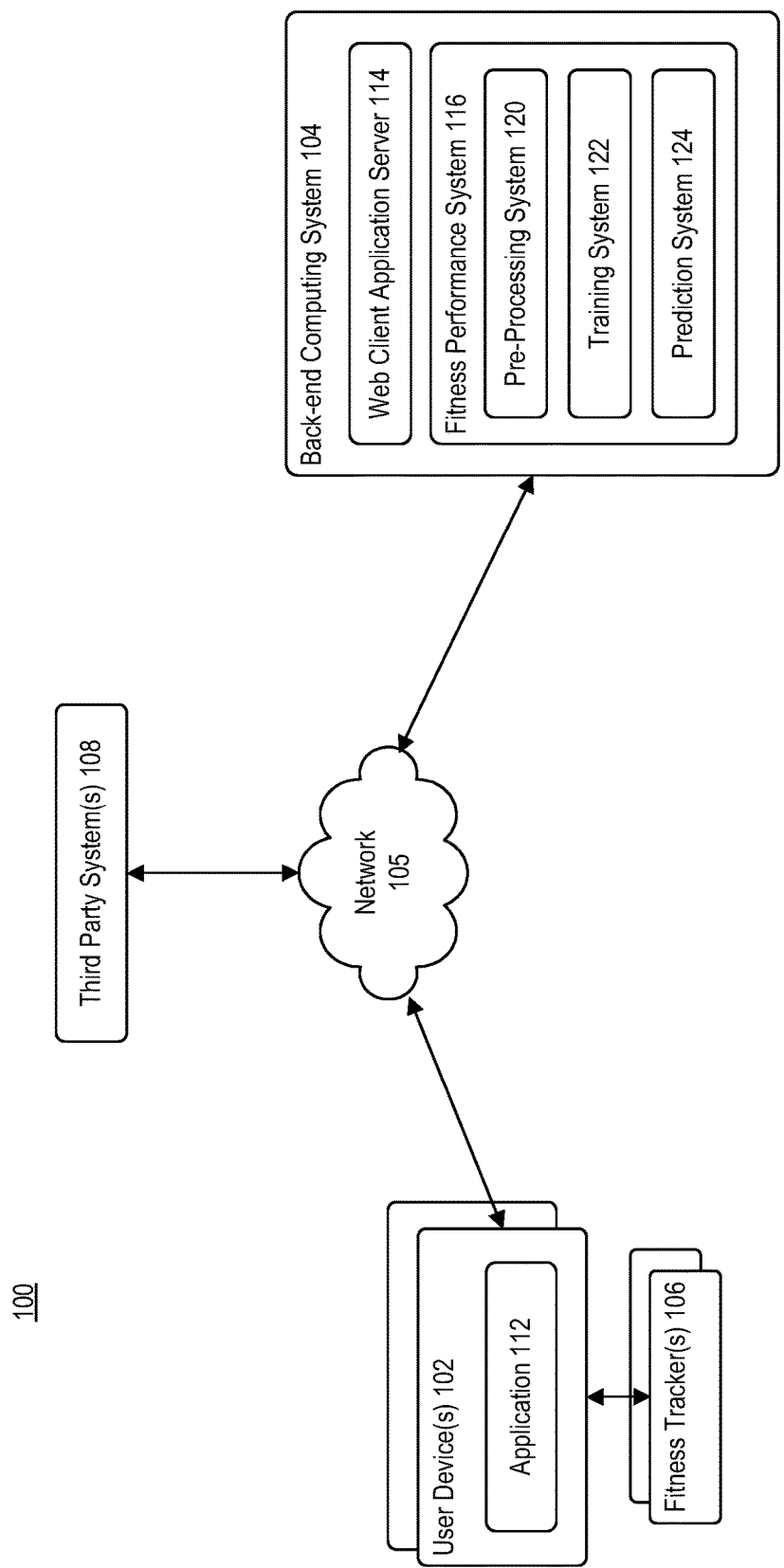
FIG. 1 is a block diagram illustrating an exemplary computing environment, according to example embodiments.

FIG. 1 is a block diagram illustrating an exemplary computing environment 100, according to example embodiments. Computing environment 100 may include at least one or more user devices 102, a back-end computing system 104, and a fitness tracking device 106 communicating via network 105.

Network 105 may be of any suitable type, including individual connections via the Internet, such as cellular or Wi-Fi networks. In some embodiments, network 105 may connect terminals, ser-vices, and mobile devices using direct connections, such as radio frequency identification (RFID), near-field communication (NFC), Bluetooth™, low-energy Bluetooth™ (BLE), Wi-Fi™ ZigBee™, ambient backscatter communication (ABC) protocols, USB, WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 105 may include any type of computer networking arrangement used to exchange data. For example, network 105 may be the Internet, a private data network, virtual private network using a public network and/or other suitable connection(s) that enables components in computing environment 100 to send and receive information between the components of computing environment 100.

User device 102 may be operated by a user. User device 102 may be representative of a mobile device, a tablet, a desktop computer, or any computing system having the capabilities described herein. User device 102 may be in communication with a fitness tracking device 106. In some embodiments, user device 102 may be in communication with fitness tracking device 106 via one or more wired or wireless connections, such as, but not limited to, a Bluetooth connection.

In operation, when a user utilizes fitness tracking device 106, fitness tracking device 106 may be configured to record a user's movements during the activity. In some embodiments, fitness tracking device 106 may record various data and save that data in a file that corresponds to the activity or workout. In some embodiments, the various data in the file may include coordinate information (e.g., timestamp, latitude coordinates, longitude coordinates) based on movements of the user during the activity or workout. In some embodiments, the various data in the file may further include one or more metrics associated with the workout such as, but not limited to, elevation, heartrate, cadence, device temperature, and the like. In some embodiments, the one or more metrics may be associated with each set of coordinate information. For example, assuming that the activity file includes three sets of coordinates ($lat_1$,$long_1$) ($lat_2$,$long_2$), ($lat_3$,$long_3$), each set of coordinates may include a set of metrics (e.g., elevation, heartrate, cadence, device temperature, etc.) associated therewith.

In some embodiments, the activity file may take the form of a GPS exchange format (GPX) file type, an interoperable data transfer (FIT) file format, a training center XLM format, a keyhole markup language format, and the like.

Fitness tracking device 106 may generate an activity file in one of these file formats upon completion of an activity or workout.

User device 102 may include at least application 112. Application 112 may be representative of an application associated with back-end computing system 104. In some embodiments, application 112 may be a standalone application associated with back-end computing system 104. In some embodiments, application 112 may be representative of a web browser configured to communicate with back-end computing system 104. In some embodiments, user device 102 may communicate over network 105 to request a webpage, for example, from web client application server 114 of back-end computing system 104. For example, user device 102 may be configured to execute application 112 to access an estimated fitness performance for the user generated by back-end computing system 104. For example, via application 112, a user can access and view their estimated fitness performance generated by back-end computing system 104 for an upcoming activity or workout. Via application 112, the user can further access and view their historical fitness performance maintained by back-end computing system 104.

The content that is displayed to user device 102 may be transmitted from web client application server 114 to user device 102, and subsequently processed by application 112 for display through a graphical user interface (GUI) of user device 102.

Back-end computing system 104 may include web client application server 114 and fitness performance system 116. Fitness performance system 116 may be configured to project or estimate a fitness performance of a user for an upcoming activity or workout based on historical activity data of the user. For example, given details of an upcoming workout or activity, fitness performance system 116 may be configured to generate a predicted activity file for that workout or activity based on the learned information about the user.

Fitness performance system 116 may include pre-processing system 120, training system 122, and prediction system 124. Each of pre-processing system 120, training system 122, and prediction system 124 may be comprised of one or more software modules. The one or more software modules are collections of code or instructions stored on a media (e.g., memory of back-end computing system 104) that represent a series of machine instructions (e.g., program code) that implements one or more algorithmic steps. Such machine instructions may be the actual computer code the processor of back-end computing system 104 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

Pre-processing system 120 may be configured to process activity records received from user devices 102 and/or fitness tracking devices 106. For example, pre-processing system 120 may be configured to perform two by-product collections of activity records to be stored in a database. In some embodiments, the activity records may include post-massaged activity records and training ready activity records.

Pre-processing system 120 may be configured to generate post-massaged activity records based on raw activity data received from user device 102 and/or fitness tracking devices 106. Pre-processing system 120 may store the post-massaged activity records for rapid retrieval by end users wishing to view analytics of their activities via application 112.

Pre-processing system 120 may further be configured to generate training ready activity records for training prediction models of fitness performance system 116. Training-ready activity records may be representative of activity records that have been processed or "post-massaged" by pre-processing system 120 in a way suitable for feeding directly into model training. Training-ready activity records may prevent fitness performance system 116 from performing repetitive computations because the training-ready activity records can be combined as-is with newer, first-time activities to update or retrain the models.

Training system 122 may be configured to train prediction models of fitness performance system 116. In some embodiments, training system 122 may train the prediction models based on athlete specific data and athlete agnostic data. In this manner, training system 122 can generate a robust suite of prediction models based on the aggregated wisdom of the broader user or athlete community.

Prediction system 124 may be configured to generate a predicted performance of the user for an upcoming activity or workout based on the training process. For example, prediction system 124 may include a suite of prediction models, each trained to project various performance metrics at one or more points of the activity or workout.

In some embodiments, computing environment 100 may further include one or more third party systems 108. In some embodiments, one or more third party systems 108 may be representative of various mapping systems or services, such as, but not limited to Google Maps and Open Street Maps. In some embodiments, one or more third party systems 108 may be representative of various weather services for obtaining weather or climate information of a given location.

Figure 2A:
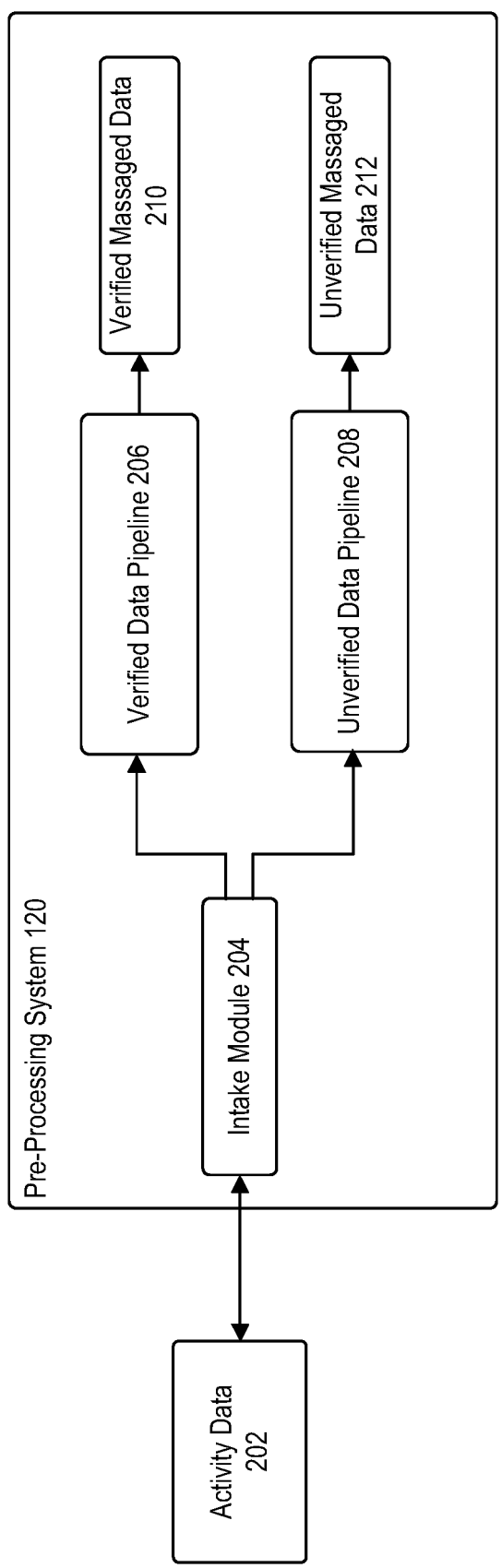
FIG. 2A is a block diagram illustrating a pre-processing system, according to example embodiments.

FIG. 2A is a block diagram illustrating pre-processing system 120, according to example embodiments. Pre-processing system 120 may be configured to filter incoming activity data 202 (e.g., device activity records) in a manner that is suitable for training the suite of prediction models. For example, pre-processing system 120 may be configured to annotate incoming activity data 202 with features relevant to performance modeling.

Pre-processing system 120 may implement a dual data massage pipeline due to the relative commonality of omissions and/or errors in raw activity data. For example, an athlete's heart rate monitor chest strap could come loose mid-training, which may result in leaving their heart rate effort data nullified. In another example, imprecise GPS signals could cause extreme drifts in location. Because manufacturers of fitness tracking devices 106 handle irregular data points in a black-box fashion, inconsistently at best and unmodified with severe consequences at worst, pre-processing system 120 may clean the raw activity data prior to model training.

Pre-processing system 120 may pre-process or massage the raw activity data in two pipelines— a first pipeline (verified data pipeline 206) for supporting historical activity records (Massage-Verified) and a second pipeline (unverified data pipeline 208) to support generic activities coming into prediction from an unknown source (Massage-Unverified). In verified data pipeline 206, verified activities performed by the athlete may be presumed to have originated from an athlete's own authenticated device or by explicit upload directly to application 112. As output from verified data pipeline 206, pre-processing system 120 may generate verified massaged data 210, which may be a pre-processed or massaged version of the raw verified data. Verified massaged data 210 may be stored in an annotated database. In this manner, features of interest that are available for input into model training, may also be viewed by athletes in an isolated context to show metrics like distance, location, weather, where/when/duration of breaks, etc.

In contrast to verified activity data, unverified activities typically provide no guarantees as to the validity of timestamps or the attribute data (e.g., heart rate) and are only intended to be used in prediction system 124. Accordingly, pre-processing system 120 may utilize unverified data pipeline 208 to process unverified activity data.

In operation, intake module 204 may be configured to decipher between verified data and unverified data. Activity data may be deemed verified data if the activity data is uploaded directly from an athlete's own authenticated device or is explicitly declared as an athlete's own activity by a manual file upload. Unverified data may refer to all other activity that is not verified by the athlete. While verified data may be used to train the various prediction models, unverified data may only be used to massage activities for prediction. Based on the determination, intake module 204 may input the subset of verified data into verified data pipeline 206 to generate verified massaged data 210. Similarly, intake module 204 may further input the subset of unverified data into unverified data pipeline 208 to generate unverified massaged data 212.

Intake module 204 may be configured to receive or import raw activity data from fitness tracking devices 106 and/or user device 102. From the raw activity data, intake module 204 may be configured to identify core features. Core features may include, but are not limited to, timestamp, latitude, longitude, elevation, heart rate, cadence, and device temperature. While the raw activity data may include additional attributes, such as, but not limited to, device information, activity name, activity description, and sport type, intake module 204 may store such additional attributes as metadata for additional activity context when available. Latitude, longitude, and elevation may be used downstream to construct a geolocation polyline to represent the traveled path of the activity.

In some embodiments, intake module 204 may be configured to generate secondary features from the core device features. Exemplary secondary features may include, but is not limited to, elevation ascent and descent of the athlete, i.e., vertical shift, trajectory against true north, relative trajectory change between location points, and gait transitions such as a shift from walking to running (or running to walking).

For example, consider an athlete running on a flat road with a barometer-enabled smartwatch recording the activity. Due to the relatively sensitive nature of a barometer's air pressure measurements, minor centimeter-range variations may be discernable as device position on the wrist bobs up and down, lifts over the head for a stretch, or hovers near the ground as shoes are tied. To account for this, intake module 204 may leverage a developer defined "threshold." For example, a developer may dictate that a climb of two meters needs to occur consistently over a distance of ten meters before it is added to the total elevation gain.

Consider, for example, a first elevation measurement as the golden reference point, from which upper and lower control limits (UCL and LCL) may be decided by an empirically derived fixed number of meters away. As far as the elevation measurements stay within these limits, the vertical shift ascent and descent will be considered zero. However, once one of the two thresholds is exceeded, such as in an ascent transition in the case of the UCL and a descent transition in the case of the LCL, intake module 204 may perform a buffered lookback to find the leading transition point from where the ascent or descent began. Intake module 204 may mark the leading transition point as the new reference point. If intake module 204 fails to find where the change of direction began in the buffered lookback, intake module 204 may consider the most recent point as the new reference. Within a given flat, ascent, or descent domain, the relative change against the reference point may be considered as vertical athlete movement. In addition, in the event an ascent or descent domain may transition into a region where slope steepness falls below a nearly-level threshold, then intake module 204 may reset the domain back to flat.

Such approach may not be limited to the micro scale of a few meters (i.e., the recording device's variable position). Instead, intake module 204 may apply the same methodology at a macro scale to gain an understanding of peaks and valleys along an activity course with UCL and LCL set at a larger range of meters. Not only is this useful as a model training input feature since an athlete is more likely to rest at the top of a peak than on a descent, but it may enable relevant prominences between the previous peak/valley and the next valley/peak to be quantifiable as well. In other words, athlete patterns regarding effort, rest, etc. can be gleamed from the prominence of a climb, the relative completion percentage along the way, the eventual high point elevation, and how steep it is.

Vertical shift against the horizontal plane may result in variable energy expenditure referred to as metabolic cost (MC), primarily influenced by gravity, and secondarily influenced by gait. To this extent the breakdown of horizontal distance travelled during each respective ascent and descent is carried forward such that MC can be calculated in the event of downstream point aggregation.

In some embodiments, intake module 204 may be further configured to generate derivative features. Intake module 204 may generate the derivative features based on the core device features and secondary features. Derivative features may broadly be categorized into subsets related to heart rate, rest duration, sun altitude and position (day, night, sunrise, etc.), speed, and slope gradient. In addition, derivative features may include cumulative totals amongst the three feature sets (e.g., total horizontal distance travelled so far).

FIG. 2B is a block diagram illustrating verified data pipeline 206 in more detail, according to example embodiments. As shown, verified data pipeline 206 may include a plurality of operations performed by pre-processing system 120.

At block 240, pre-processing system 120 may remove outliers from the activity data. Generally, sensors are susceptible to erroneous measurement. Pre-processing system 120 may identify outliers from various data, such as, but not limited to GPS location data, elevation data, speed data, and heart rate data, etc. In some embodiments, if pre-processing system 120 determines that a feature is found to be an outlier at a particular timestamp point, pre-processing system 120 may purge the entire set of data associated with that point from the activity record. In some embodiments, the exception to this rule may occur when only the HR feature is found to be an outlier. In such embodiments, pre-processing system 120 may mask the HR feature with a null value instead of purging the entire set of data associated with that point.

The intent of purging outliers in their entirety is to reduce the impact on the rest of the activity data since there is no meaningful way to calculate valid replacement values. The bar for outlier identification may be kept somewhat conservative to avoid removal overreach, and downstream filtering in later stages is expected to smooth the remaining wrinkles.

With respect to location outliers, pre-processing system 120 may be configured to remove outliers in both the horizontal and vertical planes. Pre-processing system 120 may identify clusters of outlier locations where location deviates significantly in location and/or distance from prior and subsequent points to the cluster, and where the total activity distance would shorten as a result of its removal. In some embodiments, pre-processing system 120 may use a DBSCAN (DBSCAN) clustering algorithm to identify clusters.

With respect to speed outliers, pre-processing system 120 may calculate a speed outlier value by normalizing the elapsed speed Poisson distribution through a Yeo-Johnson power transform. Pre-processing system 120 may then generate an alternate speed from dividing horizontal distance by the summation of elapsed time and a given epsilon value. Pre-processing system 120 may then mark any alternate speed greater than outlier value for removal. Pre-processing system 120 may use a slower, alternate speed as the selection criteria because points captured at low-second intervals are inherently variable and result in over-removal.

With respect to heart rate outliers, heart rate monitor devices are typically susceptible to wireless connectivity and electrode-contact loss resulting in dropped data points, sudden drops in measurement, or HR lock at the last measured value until end of the activity. In some embodiments, optical heart rate devices may be sensitive to light contamination and may enter a lock phase on the athlete's running cadence that may result in abnormally high values, or falsely locked values for extended periods of time. Pre-processing system

120 may identify clusters of locked values where measurements may remain unchanged over a minimum number of continuous samples. In some embodiments, pre-processing system 120 may use a hierarchical DBSCAN (HDBSCAN) clustering algorithm to identify clusters.

At block 242, pre-processing system 120 may smooth the activity data following removal of the outliers. For example, while outlier removal is typically expected to prune most instances of suspect points from the activity record, pre-processing system 120 may perform a filtering process to smooth out minor deficiencies related to measurement variability (i.e., noise). In contrast to outlier removal, however, during the smoothing process, pre-processing system 120 may replace existing values of features with new values, without removing the data point in its entirety. For example, pre-processing system 120 may use a Kalman filter to smooth the activity data.

At block 244, pre-processing system 120 may identify rest locations and duration of a rest for a given athlete. For example, pre-processing system 120 may use a clustering technique in which groups of consecutive timestamp points are aggregated together when the athlete is resting (i.e., not moving). Such clustering may be used to differentiate an activity's elapsed (i.e., wall-clock) time from potentially shorter duration moving time, which may be used as an indicator of effort. In some embodiments, pre-processing system 120 may use a DBSCAN (DBSCAN) clustering algorithm or Inertial Measurement Unit (IMU) to identify clusters.

At block 246, pre-processing system 120 may create a geolocation representation of the activity data by creating a buffered polygon encompassing all location points, for example within one hundred meters of the activity This representation may serve as the regional scope of annotation. For example, if an activity is fully contained within New York's Central Park, then fitness performance system 116 should only be downloading road network graphs from the immediate area, plus an additional buffer around the immediate area to account for errors in GPS data or map accuracy.

At block 248, pre-processing system 120 may annotate the geolocation representation of the activity data. The annotation process may include road and trail networks annotation, point of interest annotation, and climate annotation.

With respect to road and trail networks annotation, road and trail networks may be a useful source of an activity's metadata. Pre-processing system 120 may be configured to store the road and trail networks in a graph, represented by collections of nodes (vertices/junctions) and edges (node pairings). The graphs may not only hold attributes regarding surface conditions (e.g., paved/unpaved) that indicate how quickly an athlete can move, but may also describe the surrounding environment's complexity, and by extension where and how long an athlete may rest, voluntarily or involuntarily. However, unlike travel by vehicle that is mostly linear in direction, human powered activity can appear relatively erratic in comparison and therefore requires a series of inferences about the network to assign correct usage. The inferred feature set informs the surface type (e.g., road vs trail), road junctions (e.g., traffic signals), trail junctions, and transition nodes between surfaces (e.g., changing from paved street to trail). In some embodiments, pre-processing system 120 may capture the type of each junction and the globally unique identifier of each junction.

Exemplary paved annotations may include, but are not limited to, paved, asphalt, chipseal, concrete, concrete lanes, concrete plates, paving stones, sett paving, unhewn cobblestone, cobblestone, metal, wood, and the like. Exemplary unpaved annotations may include, but are not limited to, unpaved, compacted, fine gravel, gravel, rock, pebblestone, ground, dirt, earth, grass, grass paver, mud, sand, woodchips, salt, and the like.

Points of interest (POI) annotations may identify where the activity record comes into proximity of a man-made landmark or natural feature. The presence of these POIs may hold attributes relevant to the speed or rest of athletes and are particularly likely locations of abnormally long rest stops.

Climate annotations may be used to transpose weather related environmental conditions onto corresponding activity records. In some embodiments, pre-processing system 120 may adjust the climate annotations for elevation. In some embodiments, to generate the climate annotations, pre-processing system 120 may leverage one or more third party systems 108 for the climate metadata. In some embodiments, pre-processing system 120 may utilize device records (e.g., fitness tracking device 106) for temperature data. Exemplary climate annotations may take into account one or more of temperature, humidity, elevation, wind speed, air quality, snow cover, and the like.

As output, pre-processing system 120 may generate verified massaged data 210 that may be processed and annotated with information used to train the prediction models.

FIG. 2C is a block diagram illustrating unverified data pipeline 208 in more detail, according to example embodiments. As shown, unverified data pipeline 208 may include a plurality of operations performed by pre-processing system 120.

At block 260, pre-processing system 120 may remove athlete specific metrics from the unverified activity data. For example, pre-processing system may force athlete-specific features (e.g., HR, cadence, etc.) to a null value to avoid any potential for such attributes to contaminate the prediction seed conditions, or to confuse the user. Such process is performed because it may not be practical to guarantee the source of the activity. For example, the activity data may have been generated by different individual.

At block 262, pre-processing system 120 may set the athlete's speed for the activity data. For example, as discussed above, pre-processing system 120 may override activity speed in massage-unverified pipeline 208 to provide a consistent set of time-dependent features into prediction. Courses drawn on mapping services like GaiaGPS or AllTrails often have incoherent timestamps or a lack of timestamps altogether. Pre-processing system 120 may initialize speed to a reasonable value because other features, such as time-of-day and weather conditions, may depend on the athlete's speed. In some embodiments, pre-processing system 120 may set a normal walking speed for adults (e.g., 1.4 m/s) as the initial condition. Such setting of speed may allow for a quicker convergence in activity prediction. Because most activities are completed on a short time window of less than one day, the initial condition may not cause the prediction to diverge wildly from actual behavior.

At block 264, pre-processing system 120 may remove outliers from the activity data. Generally, sensors are susceptible to erroneous measurement. Pre-processing system 120 may identify outliers from various data, such as, but not limited to GPS location data, elevation data, etc. Unlike in verified data pipeline 206, pre-processing system 120 may not remove speed outliers or heart rate outliers from the activity data.

In some embodiments, if pre-processing system 120 determines that a feature is found to be an outlier at a particular timestamp point, pre-processing system 120 may purge the entire set of data associated with that point from the activity record.

The intent of purging outliers in their entirety is to reduce the impact on the rest of the activity data since there is no meaningful way to calculate valid replacement values. The bar for outlier identification may be kept somewhat conservative to avoid removal overreach, and downstream filtering in later stages is expected to smooth the remaining wrinkles.

With respect to location outliers, pre-processing system 120 may be configured to remove outliers in both the horizontal and vertical planes.

At step 266, pre-processing system 120 may break excessive distances in the activity data into smaller segments. For example, Point-to-point distance may be limited to a maximum distance in massage unverified pipeline 208. The purpose for doing so is to ensure downstream inputs to activity prediction may not exceed the distance characterization range during model training, as it potentially makes predictions more unreliable. Therefore, any single measurement exceeding the predefined maximum distance may be split into n straight-line segments of equal distance. This scenario is common in map-drawn activity courses because the providers of these services often simplify course geometries as much as possible to reduce the number of points, and by extension their memory footprint.

When single points are split into multiple points, pre-processing system 120 may linearly interpolate the latitude, longitude, and elevation features along the segments. Any other features, such as HR, may remain unmodified because it is unknown what the actual values should be in relation to the split location(s), and therefore would be invalid to assume.

Such process may not be part of massage verified pipeline 206 because excessive point-to-point distances in athlete activities may typically be attributed to a form of measurement error, long stretches where location is not measured (e.g., tunnels), or an athlete pausing their activity and forgetting to resume until they have already travelled some distance away. Such data may not be useful for training the prediction models due to the poor resolution of data-per-meter travelled. Leaving the point-to-point distances unmodified in massage verified pipeline 206 may allow for statistical analysis to annotate them as outliers in block 248 of verified data pipeline 206.

At block 268, pre-processing system 120 may smooth the activity data following removal of the outliers. For example, while outlier removal is typically expected to prune most instances of suspect points from the activity record, pre-processing system 120 may perform a filtering process to smooth out minor deficiencies related to measurement variability (i.e., noise). In contrast to outlier removal, however, during the smoothing process, pre-processing system 120 may replace existing values of features with new values, without removing the data point in its entirety. For example, pre-processing system 120 may use a Kalman filter to smooth the activity data.

At block 270, pre-processing system 120 may identify rest locations and duration of a rest for a given athlete. For example, pre-processing system 120 may use a clustering technique in which groups of consecutive timestamp points are aggregated together when the athlete is resting (i.e., not moving). Such clustering may be used to differentiate an activity's elapsed (i.e., wall-clock) time from moving time, which may be used as an indicator of effort.

At block 272, pre-processing system 120 may create a geolocation representation of the activity data.

At block 274, pre-processing system 120 may annotate the geolocation representation of the activity data. The annotation process may include road and trail networks annotation, point of interest annotation, and climate annotation.

With respect to road and trail networks annotation, road and trail networks may be a useful source of an activity's metadata. Pre-processing system 120 may be configured to store the road and trail networks in a graph, represented by collections of nodes (vertices/junctions) and edges (node pairings). The graphs may not only hold attributes regarding surface conditions (e.g., paved/unpaved) that indicate how quickly an athlete can move, but may also describe the surrounding environment's complexity, and by extension where and how long an athlete may rest, voluntarily or involuntarily. However, unlike travel by vehicle that is mostly linear in direction, human powered activity can appear relatively erratic in comparison and therefore requires a series of inferences about the network to assign correct usage. The inferred feature set informs the surface type (e.g., road vs trail), road junctions (e.g., traffic signals), trail junctions, and transition nodes between surfaces (e.g., changing from paved street to trail). In some embodiments, pre-processing system 120 may capture the type of each junction and the globally unique identifier of each junction.

Exemplary paved annotations may include, but are not limited to, paved, asphalt, chipseal, concrete, concrete lanes, concrete plates, paving stones, sett paving, unhewn cobblestone, cobblestone, metal, wood, and the like. Exemplary unpaved annotations may include, but are not limited to, unpaved, compacted, fine gravel, gravel, rock, pebblestone, ground, dirt, earth, grass, grass paver, mud, sand, woodchips, salt, and the like.

Points of interest (POI) annotations may identify where the activity record comes into proximity of a man-made landmark or natural feature. The presence of these POIs may hold attributes relevant to the speed or rest of athletes and are particularly likely locations of abnormally long rest stops.

Climate annotations may be used to transpose weather related environmental conditions onto corresponding activity records. In some embodiments, pre-processing system 120 may adjust the climate annotations for elevation. In some embodiments, to generate the climate annotations, pre-processing system 120 may leverage one or more third party systems 108 for the climate metadata. In some embodiments, pre-processing system 120 may utilize device records (e.g., fitness tracking device 106) for temperature data. Exemplary climate annotations may take into account one or more of temperature, humidity, elevation, wind speed, air quality, snow cover, and the like.

As output, pre-processing system 120 may generate unverified massaged data 212 that may be processed and annotated with information used as input to the prediction models.

FIGS. 3A-3F are block diagrams illustrating training system 122 in more detail, according to example embodiments. As shown across FIGS. 3A-3F, six separate performance models may be created during the training pipeline. The six separate performance models may include duration model 308, heart rate (HR) model 318, maximum HR (max HR) model 328, typical HR model 338, minimum HR (min HR) model 348, and seed HR model 358. Duration model 308, HR model 318, and seed HR model 358 may be used by prediction system 124 to make an activity prediction when the desired effort level is known. Max HR model 328, typical HR model 338, and min HR model 348 may be used when profiling the range of potential effort.

Training system 122 may generally include pre-processing module 302. Pre-processing module 302 may be configured to perform one or more pre-processing operations to the output data from verified massage pipeline 206.

In some embodiments, pre-processing module 302 may be configured to simplify the data from verified data pipeline. For example, pre-processing module 302 may remove "wiggles" common in verified massaged data 210, such that verified massaged data 210 looks reasonably close to map-drawn activities featuring straighter lines. This kind of coarse simplification is a balancing act because the more an activity is simplified, the more difficult it may be for training the models to differentiate athlete-perceptible conditions.

In some embodiments, pre-processing module 302 may be configured to compress the data. Pre-processing module 302 may utilize one or more compression methods for compressing the data. In some embodiments, pre-processing module 302 may assign points into groups of variable distance based on a gaussian distribution with a given target mean and standard deviation. In some embodiments, pre-processing module 302 may assign points into groups of variable distance based on a random distribution between a minimum and maximum distance. Compression is not meant to result in exact target distances, due to the non-uniform nature of individual points, but instead may aim for the closest possible target distance without violating minimum and maximum criteria.

The primary rationale for using randomized-distance compression methods during the model training stage is to reduce the potential for overfitting the models. At the extreme end of overfit, a model would provide nearly perfect predictions for data that it was trained with, and yet provide inferior predictions on any slight deviation, even for feature values within the training range. A secondary rationale is to enable dataset augmentation, which is the practice of modifying the same data in varying ways to enhance feature input diversity (i.e., increasing size of the sample population). This practice is common is convoluted network networks (CNN) used in image processing applications to increase the number of unique training samples. Pre-processing module 302 may achieve a similar effect of increasing the number of unique training samples by compressing the activity record into multiple permutations, each under its own grouping distance targets. Pre-processing module 302 may drop any duplicate points that may exist.

A beneficial side-effect of compression is that it substantially reduces point count, which in turn translates to reduced memory footprint, and relaxed compute requirements for model training and model serving (i.e., prediction). Furthermore, compression increases the probability that a point sent to training will have non-zero rest duration, which in turn brings more generalizable context to when and why that occurs.

In some embodiments, pre-processing module 302 may be configured to supplement an athlete's activity record if the athlete's activity record collection is insufficient in terms of points available for training (e.g., small sample size) or in terms of narrow characterization range (e.g., no diversity in sample population). In some embodiments, to supplement an athlete's activity record, pre-processing module 302 may use pre-compressed training activity records from other athletes. In some embodiments, to supplement an athlete's activity record, pre-processing module 302 may aggregate the training activity records of other athletes. For example, pre-processing module 302 may identify an athlete or athletes that are similar to the target athlete based on a combination of gender, age, and fitness level. In some embodiments, pre-processing module 302 may obfuscate the data points attribute to the other athlete or athletes.

In some embodiments, pre-processing module 302 may further annotate outliers in the data set. As those skilled in the art understand, hiding within the corpus of data about to be fed into model training are sure to be points not representative of actual performance, and thus should be removed from consideration. To identify outliers, pre-processing module 302 may be configured to utilize a variety of methods to identify statistical outliers.

Following pre-processing of the data, training modules 304-354 may be configured to train their respective machine learning models 306-356 to generate an optimized prediction model for deployment.

Figure 3A:
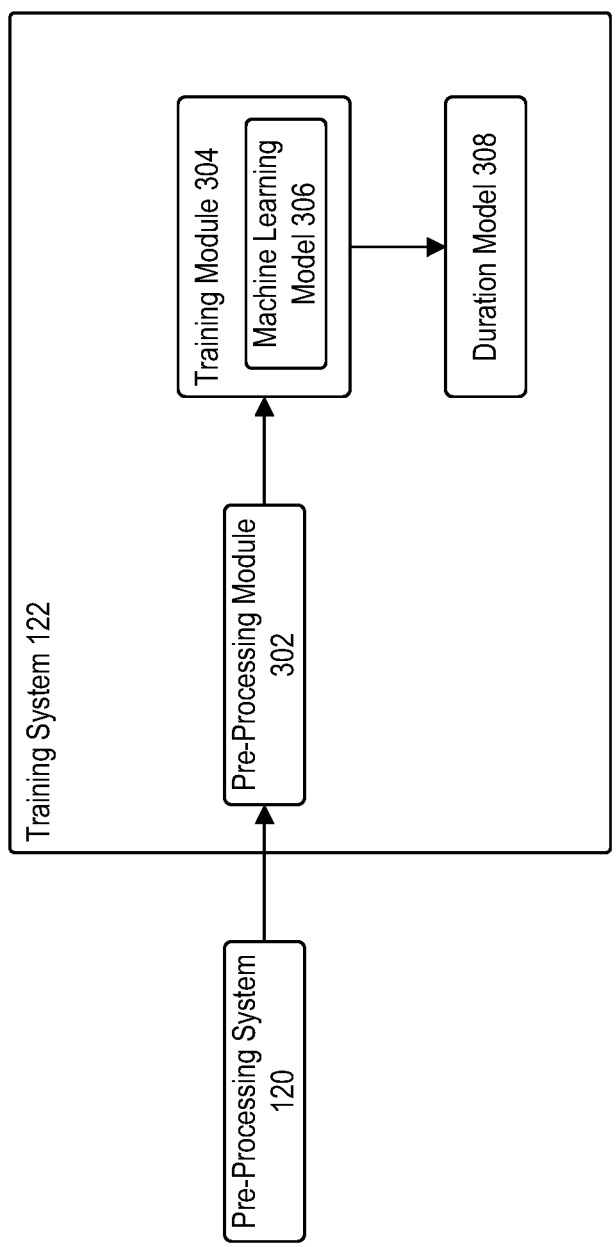
FIG. 3A is a block diagram illustrating a training system, according to example embodiments.

Referring to FIG. 3A, training module 304 may be configured to train machine learning model 306 to generate duration model 308. In some embodiments, machine learning model 306 may be representative of a deep neural network regression architecture. As those skilled in the art understand, although machine learning model 306 may be representative of a deep neural network regression architecture, other more complex architecture types may be used. For example, in some embodiments, machine learning model 306 may be representative of the long short-term memory (LSTM) variant of a recurrent neural network as it is capable of embedding feedback states into a deep neural network, thus allowing the network to learn from past long-term dependencies as it makes future predictions.

In some embodiments, such as when machine learning model 306 is representative of a deep neural network regression architecture, machine learning model 306 may include at least two hidden layers.

To train machine learning model 306, training module 304 may split the data set into three randomized groups: training, validation, and test.

In some embodiments, training module 304 may use the training group to iteratively fit batches of features to their respective outputs. In some embodiments, training module 304 may use the validation group to independently test goodness-of-fit between each of those iterations (epochs). In some embodiments, training module 304 and the test group is completely unknown by the fit process, used to test the completed model's generality. In some embodiments, the dataset may be randomized prior to split so as to combat machine learning model 306 from learning successive points of likeness.

The train-val-test process may allow for stratification of one or more explicitly requested features, equally splitting them into the three groups by their ratio against the overall sample population. For example, each activity (i.e., unique starting timestamp) may be stratified such that equal portions of its points may be allocated to the three groups, reducing the potential for activities containing many points to drown out activities with a small number of points. For example, combining a plurality of data records associated with ultramarathons with one short neighborhood run would present a needle-in-a-haystack scenario. Training module 304 may perform a similar process for ensuring equal distribution of heart rates and moving/non-moving ratios. These stratifications may effectively enforce training diversity.

In some embodiments, in addition to or instead of stratification, an even more targeted method of splitting known as oversampling is available. Oversampling isolates specific ranges of feature values into their own split process, then randomly combines their train-val-test groups together afterwards.

Training module 304 may be configured to train machine learning model 306 to generate an active time (e.g., move time+recover time) and move time based on, for example, heart rate data. In some embodiments, other input data may include, but is not limited to, information about the route corresponding to the activity, climate conditions when the activity was performed, athlete information, and the like. In some embodiments, machine learning model 306 may implement an architecture of two dense node layers with a dropout layer between the two dense node layers to reduce over-training.

Training module 304 may utilize a customized loss function that solves a fundamental problem with multi-output regression modeling, which may occur when the distributions of the outputs are significantly different. One of the outputs may have a higher loss than the other, thus resulting in spending more time optimizing the higher loss at the expense of the lower loss. Whereas moving time may be limited to the inverse of minimum human speed, active time may be at a near-zero speed, translating to hours for a hundred-meter distance. Therefore, if a standard loss function like mean squared error is used, or in this case the more appropriate Poisson, then the training optimization will inevitably skew towards active time.

The customized loss function may work by first applying a Yeo-Johnson power transform to both the true value and the predicted value of each output, bringing each separate distribution into closer alignment. The Yeo-Johnson parameters may be defined in advance during training dataset creation. The normalized distributions may then be fed into two standard loss functions, for example, two of Huber, mean absolute error, mean squared error, and/or Poisson. Training module 304 may return the mean of the two loss functions as the representative loss metric, resulting in a cleaner balance of typical scenario and tail optimization.

Following training, training module 304 may output a fully trained duration model 308 that is optimized to generate an active time and a move time.

Figure 3B:
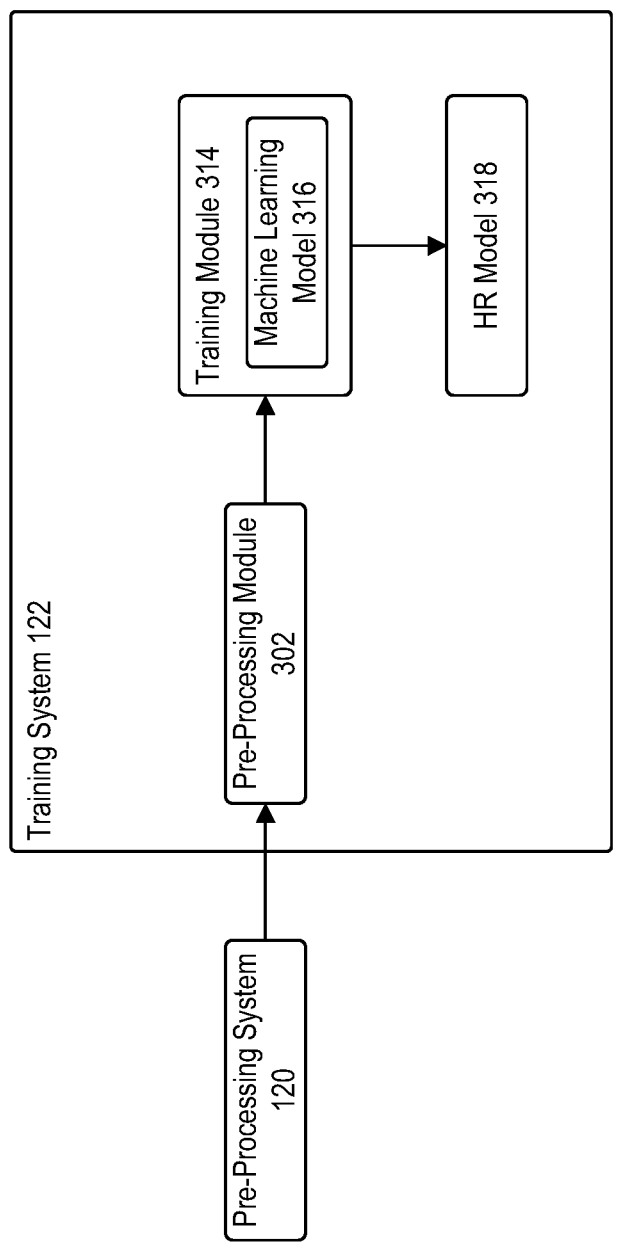
FIG. 3B is a block diagram illustrating a training system, according to example embodiments.

Referring to FIG. 3B, training module 314 may be configured to train machine learning model 316 to generate HR model 318. In some embodiments, machine learning model 316 may have a similar architecture to machine learning model 306 discussed above in conjunction with FIG. 3A. In some embodiments, machine learning model 316 may include an architecture of two dense node layers with a dropout layer in between the two dense node layers to reduce over-training risk. Training module 314 may utilize a standard mean squared error (MSE) loss during training.

Training module 314 may be configured to train machine learning model 316 to generate an athlete's heart rate and moving heart rate at various points of an activity based on one or more of an active time, a move time, a cumulative rest time, a previous point's heart rate, and the like. In some embodiments, other input data may include, but is not limited to, information about the route corresponding to the activity, climate conditions when the activity was performed, athlete information, and the like.

Following training, training module 314 may output a fully trained HR model 318 that is optimized to generate an athlete's heart rate and moving heart rate at various points of an activity.

Figure 3C:
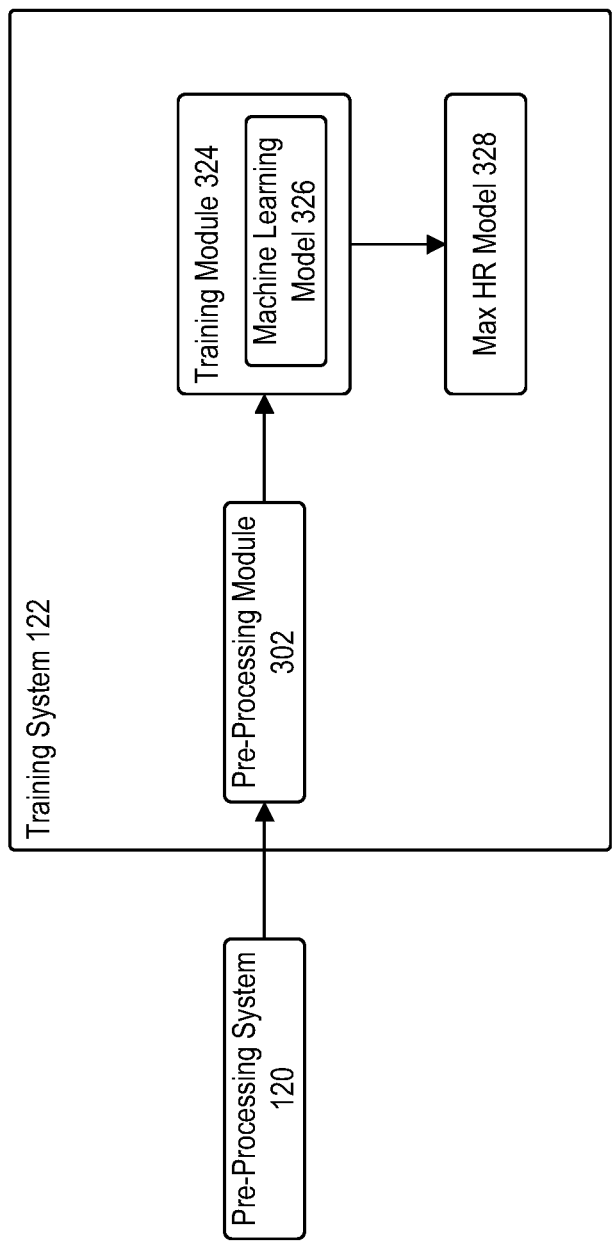
FIG. 3C is a block diagram illustrating a training system, according to example embodiments.

Referring to FIG. 3C, training module 324 may be configured to train machine learning model 326 to generate a max HR model 328. In some embodiments, machine learning model 316 may have a similar architecture to machine learning model 306 discussed above in conjunction with FIG. 3A. For example, machine learning model 306 may include an architecture of a single dense node layer to achieve a non-linear continuous function. Training module 324 may utilize a special type of quantile-based loss function called PinballLoss during training.

Training module 324 may be configured to train machine learning model 326 to generate a maximum heart rate of an athlete at various points of an activity based on time and environment features of the activity. In some embodiments, other input data may include, but is not limited to, information about the route corresponding to the activity, climate conditions when the activity was performed, athlete information, and the like.

Following training, training module 324 may output a fully trained max HR model 328 that is optimized to generate a maximum heart rate of an athlete at various points of an activity.

Figure 3D:
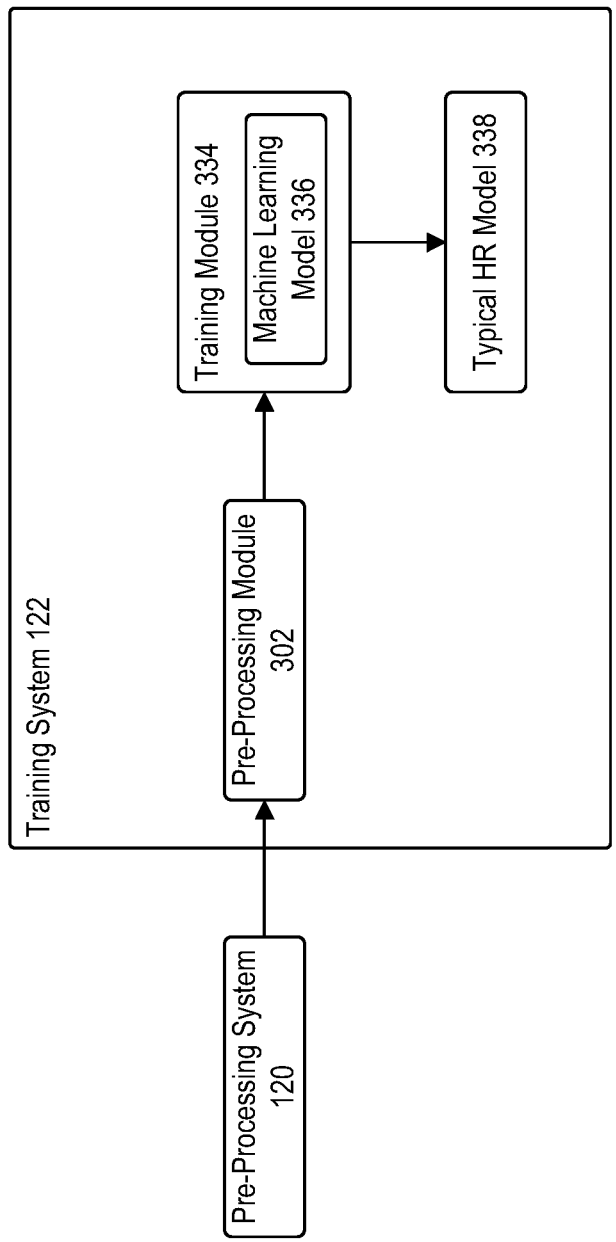
FIG. 3D is a block diagram illustrating a training system, according to example embodiments.

Referring to FIG. 3D, training module 334 may be configured to train machine learning model 336 to generate a typical HR model 338. In some embodiments, machine learning model 336 may have a similar architecture to machine learning model 306 discussed above in conjunction with FIG. 3A. For example, machine learning model 336 may implement an architecture of a single dense node layer to achieve a non-linear continuous function. Training module 334 may use a custom loss function that transforms predict and actual values through Yeo-Johnson and then returns Huber loss.

Training module 334 may be configured to train machine learning model 336 to generate a heart rate and moving heart rate of an athlete at various points of an activity based on time and environment features of the activity. In some embodiments, other input data may include, but is not limited to, information about the route corresponding to the activity, climate conditions when the activity was performed, athlete information, and the like.

Following training, training module 334 may output a fully trained typical HR model 338 that is optimized to generate a heart rate and moving heart rate of an athlete at various points of an activity.

Figure 3E:
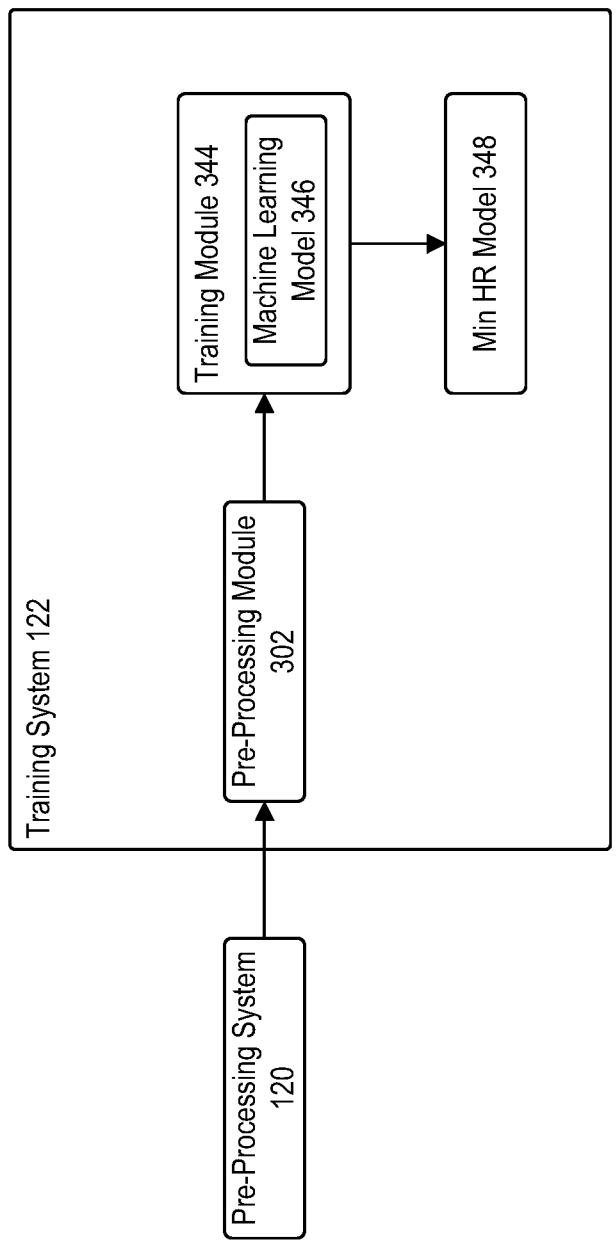
FIG. 3E is a block diagram illustrating a training system, according to example embodiments.

Referring to FIG. 3E, training module 344 may be configured to train machine learning model 346 to generate min HR model 348. In some embodiments, machine learning model 346 may have a similar architecture to machine learning model 306 discussed above in conjunction with FIG. 3A. For example, machine learning model 346 may implement an architecture of a single dense node layer to achieve a non-linear continuous function. Training module 344 may utilize a special type of quantile-based loss function called PinballLoss during training.

Training module 344 may be configured to train machine learning model 346 to generate a minimum heart rate of the athlete at various points of the activity based on time and environment features. In some embodiments, other input data may include, but is not limited to, information about the route corresponding to the activity, climate conditions when the activity was performed, athlete information, and the like.

Following training, training module 344 may output a fully trained min HR model 348 that is optimized to generate a minimum heart rate of an athlete at various points of an activity.

Figure 3F:
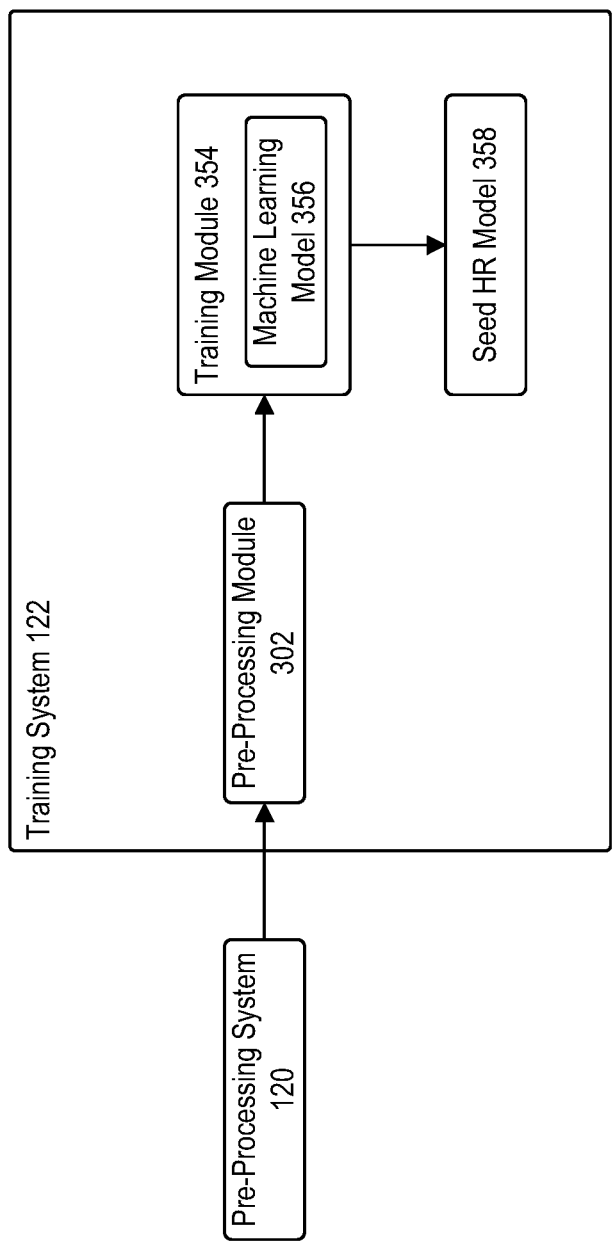
FIG. 3F is a block diagram illustrating a training system, according to example embodiments.

Referring to FIG. 3F, training module 354 may be configured to train machine learning model 356 to generate a seed HR model 358. In some embodiments, machine learning model 356 may have a similar architecture to machine learning model 306 discussed above in conjunction with FIG. 3A. For example, machine learning model 356 may implement an architecture of two dense node layers with a dropout layer in between the two dense node layers to reduce over-training risk. Training module 354 may use the customized loss function that transforms predicted and actual values through Yeo-Johnson and then returns Huber loss.

Training module 354 may be configured to train machine learning model 356 to generate a heart rate and moving heart rate of the athlete at various points of the activity based at least on the target average HR (i.e., effort level) of the activity. In some embodiments, other input data may include, but is not limited to, information about the route corresponding to the activity, climate conditions when the activity was performed, athlete information, and the like.

Following training, training module 354 may output a fully trained seed HR model 358 that is optimized to generate a heart rate and moving heart rate of the athlete. Seed HR model 358 may be the first model used in activity prediction to set the initial HR values on each point of the activity. Seed HR model 358 may be optimized to tease out the nuance of point-specific shifts in effort throughout the activity (e.g., a rise in effort when transitioning from flat gradient to uphill, or when cool morning weather shifts to the blazing heat of noon).

Figure 4:
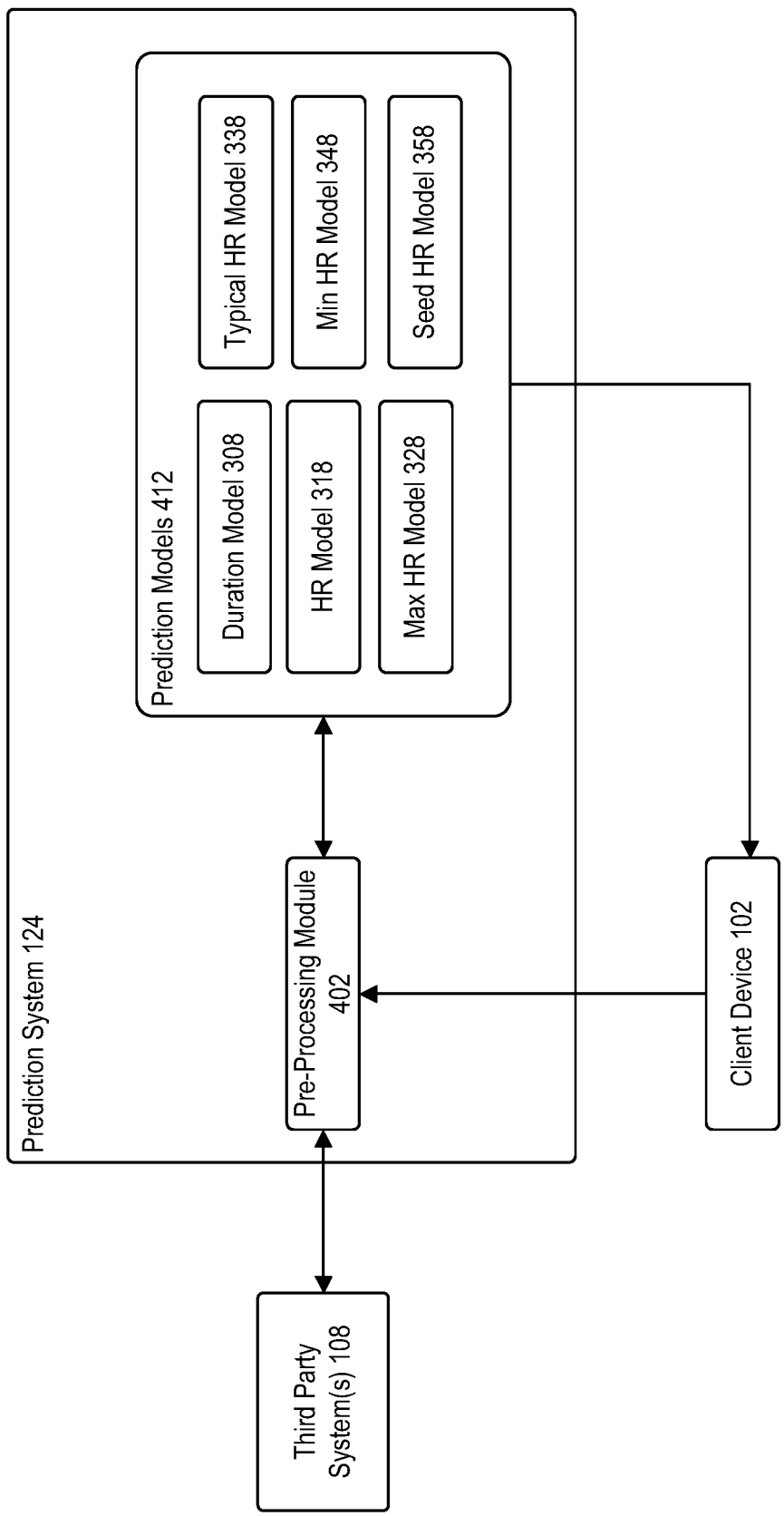
FIG. 4 is a block diagram illustrating a prediction system, according to example embodiments.

FIG. 4 is a block diagram illustrating prediction system 124 in more detail, according to example embodiments. As shown, the six models created by training system 122 may be integrated or assembled into prediction models 412 to generate an activity prediction. For example, as shown, prediction system 124 may include duration model 308, HR model 318, max HR model 328, typical HR model 338, min HR model 348, and seed HR model 358.

In some embodiments, only a subset of prediction models 412 may be used to generate an activity prediction. For example, at a minimum, prediction system 124 may use duration model 308, HR model 318, and seed HR model 358 to generate an activity prediction. In some embodiments, prediction system 124 may further use max HR model 328, typical HR model 338, and min HR model 348 for determining the range of potential heart rate efforts.

In some embodiments, when a request to generate an activity prediction for a user comes in from user device 102, pre-processing module 402 may receive the request. In some embodiments, the request may include details of the activity or workout. For example, user device 102 may provide pre-processing module 402 with route information for the upcoming activity or workout. In some embodiments, pre-processing module 402 may receive the details of the route information directly from user device 102. In some embodiments, pre-processing module 402 may retrieve the details of the route information from one or more third party systems 108, such as Open Street Map, Google maps, and the like.

In some embodiments, the request may further include a time and date of the upcoming workout. Pre-processing module 402 may communication with one or more third party systems 108 to receive or retrieve climate information for the proposed time and date of the upcoming workout.

In some embodiments, pre-processing module 402 may perform one or more pre-processing operations before providing the input data to the prediction models. For example, pre-processing module 402 may perform simplification and/or compression processes to prepare the data for input to the prediction models. In some embodiments, the simplification process and/or compression process may be similar to the simplification process and compression process discussed above in conjunction with FIG. 3A.

In the event that effort levels of the user are unknown, an activity may be profiled using max HR model 328, typical HR model 338, and min HR model 348. Such process may result in a set of predicted activities being anchored by minimum effort and maximum effort, with the typical effort of the user falling somewhere in between the minimum effort and the maximum effort. Based on the generated maximum effort, minimum effort, and typical effort, prediction system 124 may generate a stratified set of activity predictions for the user using duration model 308, HR model 318, and seed HR model 358. If, however, the effort level of the user is known or provided to prediction system 124, prediction system 124 may use duration model 308, HR model 318, and seed HR model 358 without needing max HR model 328, typical HR model 338, and min HR model 348.

Prediction system 124 may be configured to generate a multi-point prediction and a single point prediction using the prediction models. The difference between a multi-point prediction and a single point prediction is that chained multi-point activities may refresh their timestamps and derivative features prior to returning the activity, because those features are used to guide the next iteration of predictions. Single-point predictions, in contrast, may be unable to refresh these features due to a lack of cumulative point-to-point context.

As output, prediction system 124 may generate a predicted activity file for the upcoming activity. The predicted activity file may be similar to an actual activity file generated by a fitness tracking device 106. For example, at each point in the predicted activity file, prediction system 124 may generate a set of metrics, such as duration, heart rate, cadence, etc. In this manner, the user may be provided with an estimated activity profile based on the upcoming workout.

Figure 5:
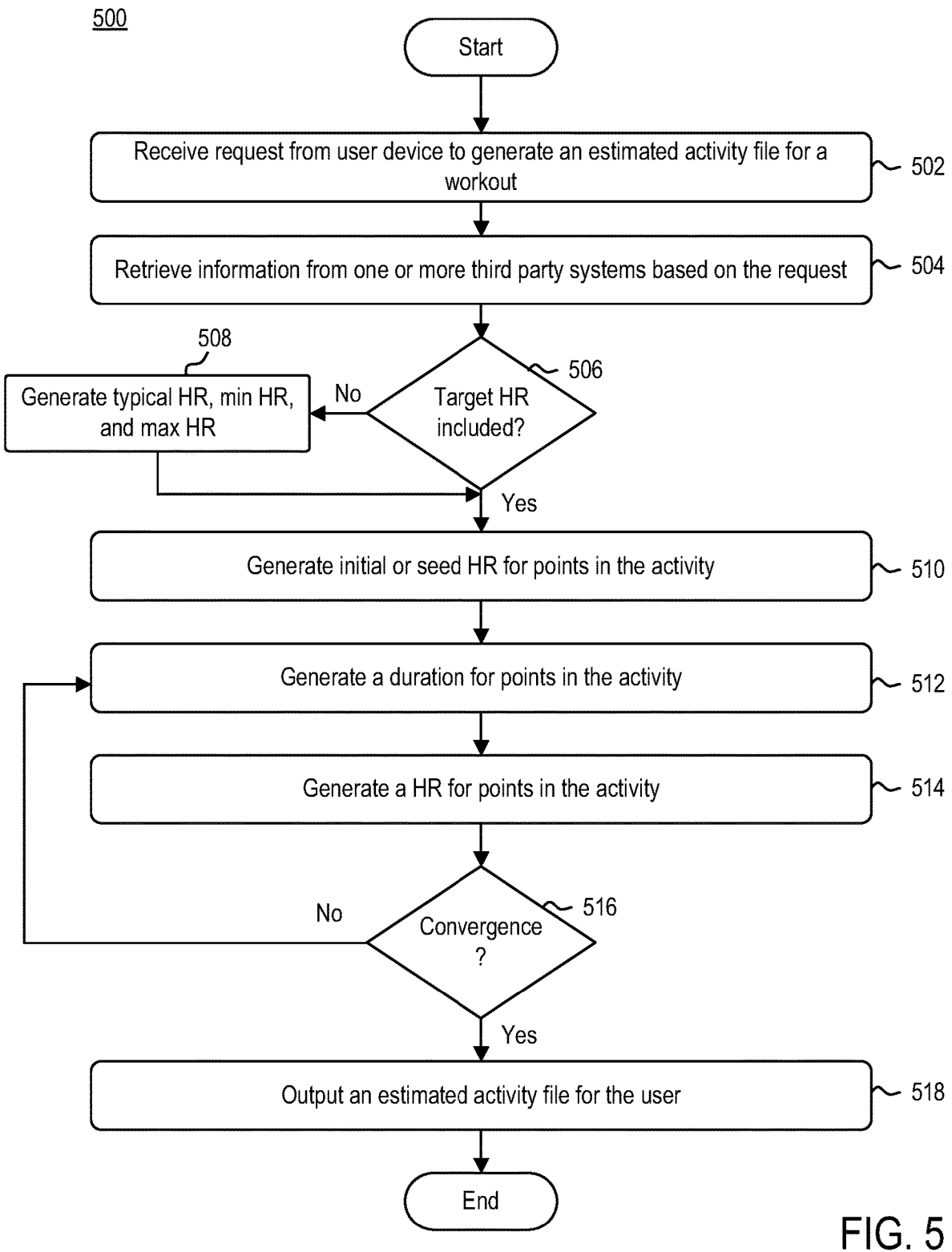
FIG. 5 is a flow diagram illustrating a method of generating an estimated activity file for a user, according to example embodiments.

FIG. 5 is a flow diagram illustrating a method 500 of generating an estimated activity file for a user, according to example embodiments. Method 500 may begin at step 502.

At step 502, back-end computing system 104 may receive a request from user device 102 to generate an estimated activity file for the user for an upcoming activity or workout. In some embodiments, the request may include an indication of a route for the activity. In some embodiments, the request may include an estimated date and time of the upcoming activity or workout. In some embodiments, the request may include a target effort level for the user. For example, the user may indicate their target heart rate for the activity or workout.

At step 504, back-end computing system 104 may retrieve information from one or more third party systems 108 based on the request. In some embodiments, based on the request, prediction system 124 may interface with one or more mapping systems to retrieve route information for the workout or activity. In some embodiments, based on the request, prediction system 124 may interface with one or more weather systems to retrieve weather related information for the workout or activity.

At step 506, back-end computing system 104 may determine whether the request includes a target heart rate for the activity or workout. If, at step 506, prediction system 124 determines that the request does not include a target heart rate, then method 500 may proceed to step 508.

At step 508, back-end computing system 104 may predict the typical heart rate, maximum heart rate, and the minimum heart rate of the user based on time and environment features of the activity. For example, prediction system 124 may use max HR model 328 to generate a maximum heartrate of the user based on the time and terrain information. Prediction system 124 may further use min HR model 348 to generate a minimum heartrate of the user based on the time and terrain information. Prediction system 124 may further use typical HR model 338 to generate a typical heartrate of the user based on the time and terrain information. The generated minimum heartrate, maximum heartrate, and typical heartrate may be used in lieu of the target heartrate for generated the predicted activity file for the workout or activity.

At step 510, back-end computing system 104 may generate an initial or seed heart rate and initial or seed moving heart rate of the athlete at each point of the activity. For example, based at least on the target average HR (i.e., effort level) of the activity or the minimum heartrate, maximum heartrate, and typical heartrate (if the target average heartrate is not provided), seed HR model 358 may generate an initial estimated heart rate and initial moving heart rate at each point of the activity or workout.

At step 512, back-end computing system 104 may generate an estimated duration of each point of the workout or activity. For example, based on the initial heart rate data generated by seed HR model 358, duration model 308 may generate an active time (e.g., move time+recover time) and move time for the workout or activity at each point of the workout or activity.

At step 514, back-end computing system 104 may generate an estimated heart rate and moving heart rate at each point of an activity based on the initial heart rate, climate information, and/or duration information. For example, HR model 318 may be configured to generate an estimated heart rate and moving heart rate at a given point of an activity based on the initial heart rate at that point of the activity, duration information of that point of the activity, and climate information at that point of the activity.

At step 516, back-end computing system 104 may determine if there is a convergence between the HR that is generated for the activity (at step 516) and the target HR. If, at step 516, prediction system 124 determines that there is not a convergence, then method 500 may revert to step 512, and prediction system 124 may generate a new duration and a new estimated heart rate for the user.

If, however, at step 516, back-end computing system 104 determines that there is a convergence, then method 500 may proceed to step 518. At step 518, back-end computing system 104 may output an estimated activity file for the user based on the predictions. For example, prediction system 124 may generate an activity profile that includes various metrics at each point of the workout or activity. The various metrics may include heartrate, duration, cadence, and the like.

Figure 6A:
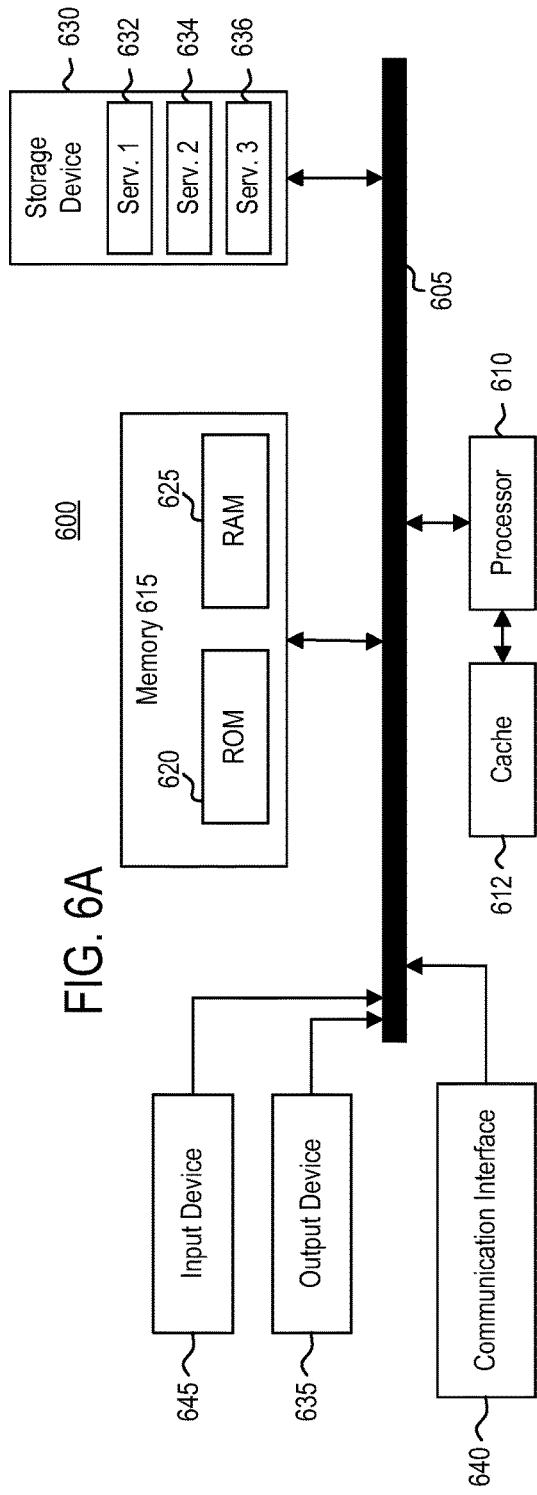
FIG. 6A is a block diagram illustrating a computing device, according to example embodiments.

FIG. 6A illustrates a system bus architecture of computing system 600, according to example embodiments. System 600 may be representative of at least a portion of user device 102 and/or back-end computing system 104. One or more components of system 600 may be in electrical communication with each other using a bus 605. System 600 may include a processing unit (CPU or processor) 610 and a system bus 605 that couples various system components including the system memory 615, such as read only memory (ROM) 620 and random access memory (RAM) 625, to processor 610. System 600 may include a cache of high-speed memory connected directly with, in close proximity to, or integrated as part of processor 610. System 600 may copy data from memory 615 and/or storage device 630 to cache 612 for quick access by processor 610. In this way, cache 612 may provide a performance boost that avoids processor 610 delays while waiting for data. These and other modules may control or be configured to control processor 610 to perform various actions. Other system memory 615 may be available for use as well. Memory 615 may include multiple different types of memory with different performance characteristics. Processor 610 may include any general purpose processor and a hardware module or software module, such as service 1 632, service 2 634, and service 3 636 stored in storage device 630, configured to control processor 610 as well as a special-purpose processor where software instructions are incorporated into the actual processor design. Processor 610 may essentially be a completely self-contained computing system, containing multiple cores or processors, a bus, memory controller, cache, etc. A multi-core processor may be symmetric or asymmetric.

To enable user interaction with the computing system 600, an input device 645 may represent any number of input mechanisms, such as a microphone for speech, a touch-sensitive screen for gesture or graphical input, keyboard, mouse, motion input, speech and so forth. An output device 635 may also be one or more of a number of output mechanisms known to those of skill in the art. In some instances, multimodal systems may enable a user to provide multiple types of input to communicate with computing system 600. Communications interface 640 may generally govern and manage the user input and system output. There is no restriction on operating on any particular hardware arrangement and therefore the basic features here may easily be substituted for improved hardware or firmware arrangements as they are developed.

Storage device 630 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 625, read only memory (ROM) 620, and hybrids thereof.

Storage device 630 may include services 632, 634, and 636 for controlling the processor 610. Other hardware or software modules are contemplated. Storage device 630 may be connected to system bus 605. In one aspect, a hardware module that performs a particular function may include the software component stored in a computer-readable medium in connection with the necessary hardware components, such as processor 610, bus 605, output device 635 (e.g., display), and so forth, to carry out the function.

Figure 6B:
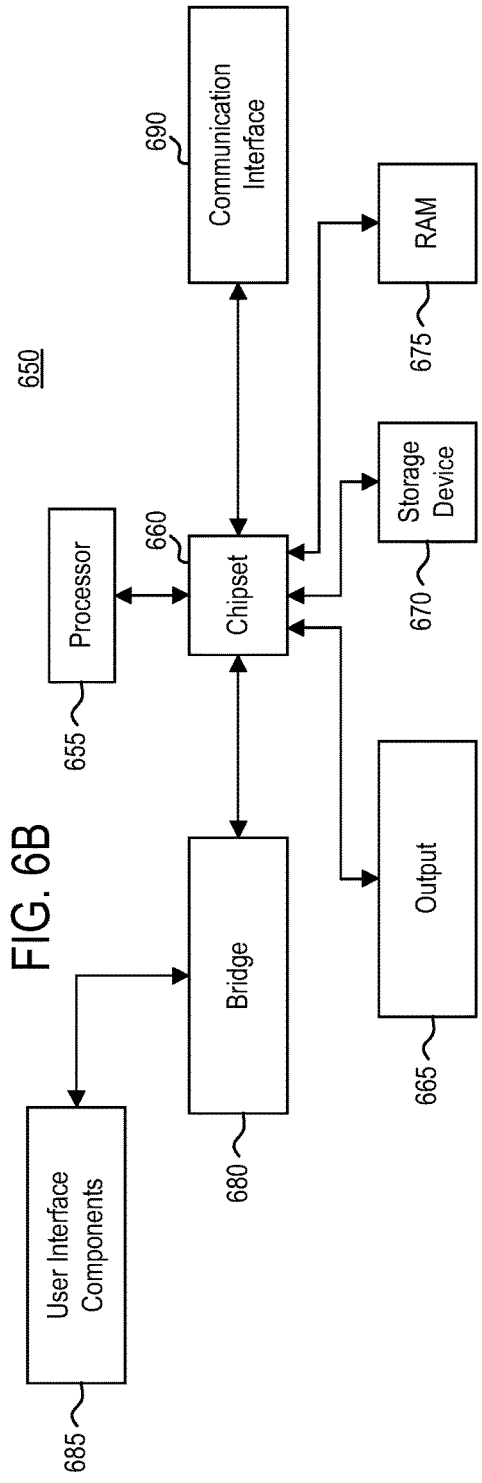
FIG. 6B is a block diagram illustrating a computing device, according to example embodiments.

FIG. 6B illustrates a computer system 650 having a chipset architecture that may represent at least a portion of user device 102 and/or back-end computing system 104. Computer system 650 may be an example of computer hardware, software, and firmware that may be used to implement the disclosed technology. System 650 may include a processor 655, representative of any number of physically and/or logically distinct resources capable of executing software, firmware, and hardware configured to perform identified computations. Processor 655 may communicate with a chipset 660 that may control input to and output from processor 655. In this example, chipset 660 outputs information to output 665, such as a display, and may read and write information to storage device 670, which may include magnetic media, and solid state media, for example. Chipset 660 may also read data from and write data to storage device 675 (e.g., RAM). A bridge 680 for interfacing with a variety of user interface components 685 may be provided for interfacing with chipset 660. Such user interface components 685 may include a keyboard, a microphone, touch detection and processing circuitry, a pointing device, such as a mouse, and so on. In general, inputs to system 650 may come from any of a variety of sources, machine generated and/or human generated.

Chipset 660 may also interface with one or more communication interfaces 690 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 655 analyzing data stored in storage device 670 or storage device 675. Further, the machine may receive inputs from a user through user interface components 685 and execute appropriate functions, such as browsing functions by interpreting these inputs using processor 655.

It may be appreciated that example systems 600 and 650 may have more than one processor 610 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A method comprising:
   receiving, by a computing system from a user device, a request to generate an estimated activity profile for a user of the user device for a workout;
   identifying, by the computing system, route information for the workout, wherein the route information comprises at least one data point associated with the route information;
   generating, by the computing system via a trained prediction system, an initial estimated heartrate for the user for the at least one data point in the route information based on a personalized training process for the user;
   generating, by the computing system via the trained prediction system, a duration of a portion of the workout based on the at least one data point in the route information and environmental information associated with a time and day of the workout;
   generating, by the computing system via the trained prediction system, a projected heartrate of the user during the workout based on the initial estimated heartrate of the user and the generated duration; and
   outputting, by the computing system, the estimated activity profile corresponding to the workout based on the projected heartrate of the user, wherein the estimated activity profile comprises the projected heartrate of the user.

2. The method of claim 1, further comprising:
   determining, by the computing system, that the request comprises a target heartrate for the workout,
   wherein generating the initial estimated heartrate for the user is further based on the target heartrate for the workout.

3. The method of claim 1, further comprising:
   determining, by the computing system, that the request does not comprise a target heartrate for the workout; and
   based on the request, generating, by the computing system a typical heartrate, maximum heartrate, and minimum heartrate for the user based on time and/or terrain features associated with the workout.

4. The method of claim 1, wherein the route information comprises at least a second data point associated with the route information.

5. The method of claim 4, further comprising:
   generating, by the computing system via the trained prediction system, a second duration of a second portion of the workout based on the at least second data point in the route information and second environmental information associated with a second time and the day of the workout; and
   generating, by the computing system via the trained prediction system, a second projected heartrate of the user during the workout based on the initial estimated heartrate of the user, the generated duration, and the second generated duration.

6. The method of claim 5, wherein outputting, by the computing system, the estimated activity profile corresponding to the workout based on the projected heartrate of the user comprises:
   generating the estimated activity profile, wherein the estimated activity profile comprises the projected heartrate of the user at the at least one data point and the second projected heartrate of the user at the at least second data point.

7. The method of claim 1, further comprising:
   determining, by the computing system, that the workout is a multi-point workout; and
   based on the determining, simplifying and compressing, by the computing system, the route information associated with the workout.

8. A non-transitory computer readable medium comprising one or more sequences of instructions, which, when executed by a processor, causes a computing system to perform operations comprising:

receiving, by the computing system from a user device, a request to generate an estimated activity profile for a user of the user device for a workout;

identifying, by the computing system, route information for the workout, wherein the route information comprises at least one data point associated with the route information;

generating, by the computing system via a trained prediction system, an initial estimated heartrate for the user for the at least one data point in the route information based on a personalized training process for the user;

generating, by the computing system via the trained prediction system, a duration of a portion of the workout based on the at least one data point in the route information and environmental information associated with a time and day of the workout;

generating, by the computing system via the trained prediction system, a projected heartrate of the user during the workout based on the initial estimated heartrate of the user and the generated duration; and outputting, by the computing system, the estimated activity profile corresponding to the workout based on the projected heartrate of the user, wherein the estimated activity profile comprises the projected heartrate of the user.

9. The non-transitory computer readable medium of claim 8, further comprising:
determining, by the computing system, that the request comprises a target heartrate for the workout,
wherein generating the initial estimated heartrate for the user is further based on the target heartrate for the workout.

10. The non-transitory computer readable medium of claim 8, further comprising:
determining, by the computing system, that the request does not comprise a target heartrate for the workout; and
based on the request, generating, by the computing system a typical heartrate, maximum heartrate, and minimum heartrate for the user based on time and/or environmental features associated with the workout.

11. The non-transitory computer readable medium of claim 8, wherein the route information comprises at least a second data point associated with the route information.

12. The non-transitory computer readable medium of claim 11, further comprising:
generating, by the computing system via the trained prediction system, a second duration of a second portion of the workout based on the at least second data point in the route information and second environmental information associated with a second time and the day of the workout; and
generating, by the computing system via the trained prediction system, a second projected heartrate of the user during the workout based on the initial estimated heartrate of the user, the generated duration, and the second generated duration.

13. The non-transitory computer readable medium of claim 12, wherein outputting, by the computing system, the estimated activity profile corresponding to the workout based on the projected heartrate of the user comprises:
generating the estimated activity profile, wherein the estimated activity profile comprises the projected heartrate of the user at the at least one data point and the second projected heartrate of the user at the at least second data point.

14. The non-transitory computer readable medium of claim 8, further comprising:
determining, by the computing system, that the workout is a multi-point workout; and
based on the determining, simplifying and compressing, by the computing system, the route information associated with the workout.

15. A system comprising:
a processor; and
a memory having programming instructions stored thereon, which, when executed by the processor, causes the system to perform operations comprising:
receiving, from a user device, a request to generate an estimated activity profile for a user of the user device for a workout;
identifying route information for the workout, wherein the route information comprises at least one data point associated with the route information;
generating, via a trained prediction system, an initial estimated heartrate for the user for the at least one data point in the route information based on a personalized training process for the user;
generating, via the trained prediction system, a duration of a portion of the workout based on the at least one data point in the route information and environmental information associated with a time and day of the workout;
generating, via the trained prediction system, a projected heartrate of the user during the workout based on the initial estimated heartrate of the user and the generated duration; and
outputting the estimated activity profile corresponding to the workout based on the projected heartrate of the user, wherein the estimated activity profile comprises the projected heartrate of the user.

16. The system of claim 15, wherein the operations further comprise:
determining that the request comprises a target heartrate for the workout,
wherein generating the initial estimated heartrate for the user is further based on the target heartrate for the workout.

17. The system of claim 15, wherein the operations further comprise:
determining that the request does not comprise a target heartrate for the workout; and
based on the request, generating a typical heartrate, maximum heartrate, and minimum heartrate for the user based on time and/or environmental features associated with the workout.

18. The system of claim 15, wherein the route information comprises at least a second data point associated with the route information.

19. The system of claim 18, wherein the operations further comprise:
generating, via the trained prediction system, a second duration of a second portion of the workout based on the at least second data point in the route information and second environmental information associated with a second time and the day of the workout; and
generating, via the trained prediction system, a second projected heartrate of the user during the workout based on the initial estimated heartrate of the user, the generated duration, and the second generated duration.

20. The system of claim 19, wherein outputting the estimated activity profile corresponding to the workout based on the projected heartrate of the user comprises:

generating the estimated activity profile, wherein the estimated activity profile comprises the projected heartrate of the user at the at least one data point and the second projected heartrate of the user at the at least second data point.

\* \* \* \* \*